United States Patent
Na

(10) Patent No.: US 10,294,495 B2
(45) Date of Patent: May 21, 2019

(54) FERMENTED MINERAL RAW-EDIBLE PILL WITH CONSTIPATION REDUCTION AND FATIGUE RECOVERY AND METHOD FOR PRODUCING THE SAME

(71) Applicant: Chin Keol Na, Yangsan-si (KR)

(72) Inventor: Chin Keol Na, Yangsan-si (KR)

( * ) Notice: Subject to any disclaimer, the term of this patent is extended or adjusted under 35 U.S.C. 154(b) by 128 days.

(21) Appl. No.: 15/195,669

(22) Filed: Jun. 28, 2016

(65) Prior Publication Data

US 2017/0002381 A1 Jan. 5, 2017

(30) Foreign Application Priority Data

Jun. 30, 2015 (KR) .................. 10-2015-0092978

(51) Int. Cl.

| | | |
|---|---|---|
| *A61K 9/20* | (2006.01) | |
| *C12P 1/04* | (2006.01) | |
| *A61K 36/03* | (2006.01) | |
| *A61K 36/04* | (2006.01) | |
| *A61K 36/07* | (2006.01) | |
| *A61K 36/11* | (2006.01) | |
| *A61K 36/40* | (2006.01) | |
| *A61K 36/42* | (2006.01) | |
| *A61K 36/46* | (2006.01) | |
| *A61K 36/48* | (2006.01) | |
| *A61K 36/88* | (2006.01) | |
| *C12R 1/125* | (2006.01) | |
| *A61K 36/899* | (2006.01) | |
| *A61K 36/8998* | (2006.01) | |
| *A61K 36/9068* | (2006.01) | |
| *A61K 36/9066* | (2006.01) | |
| *A61K 36/185* | (2006.01) | |

(52) U.S. Cl.
CPC .............. *C12P 1/04* (2013.01); *A61K 36/03* (2013.01); *A61K 36/04* (2013.01); *A61K 36/07* (2013.01); *A61K 36/11* (2013.01); *A61K 36/185* (2013.01); *A61K 36/40* (2013.01); *A61K 36/42* (2013.01); *A61K 36/46* (2013.01); *A61K 36/48* (2013.01); *A61K 36/88* (2013.01); *A61K 36/899* (2013.01); *A61K 36/8998* (2013.01); *A61K 36/9066* (2013.01); *A61K 36/9068* (2013.01); *C12R 1/125* (2013.01); *A61K 9/2059* (2013.01)

(58) Field of Classification Search
None
See application file for complete search history.

(56) References Cited

FOREIGN PATENT DOCUMENTS

| KR | 10-2007-0078345 A | | 7/2007 |
|---|---|---|---|
| KR | 10-2009-0014033 A | | 2/2009 |
| KR | 20120103917 | * | 9/2012 |
| KR | 10-1246577 | * | 3/2013 |
| KR | 10-1324733 B1 | | 11/2013 |
| KR | 10-1387190 B1 | | 4/2014 |

OTHER PUBLICATIONS

Yu at al. 1998. Bibliographical study on microorganisms of traditional Korean Nuruk (since 1945). J Korean Soc Food Sci Nutr., vol. 27, pp. 789-799. (Year: 1998).*

* cited by examiner

*Primary Examiner* — Blaine Lankford
(74) *Attorney, Agent, or Firm* — Korus Patent, LLC; Seong Il Jeong

(57) ABSTRACT

The invention relates to a method for producing a fermented mineral pill with constipation reduction and fatigue recovery, the method comprising: cultivating *Bacillus subtilis* using a rice straw; fermenting at least one of a rice-husk powder, a rice-bran powder and a lentil bean power using the *Bacillus subtilis* to acquire a fermented mixture; and shaping and drying the fermented mixture into solid pills.

5 Claims, 1 Drawing Sheet

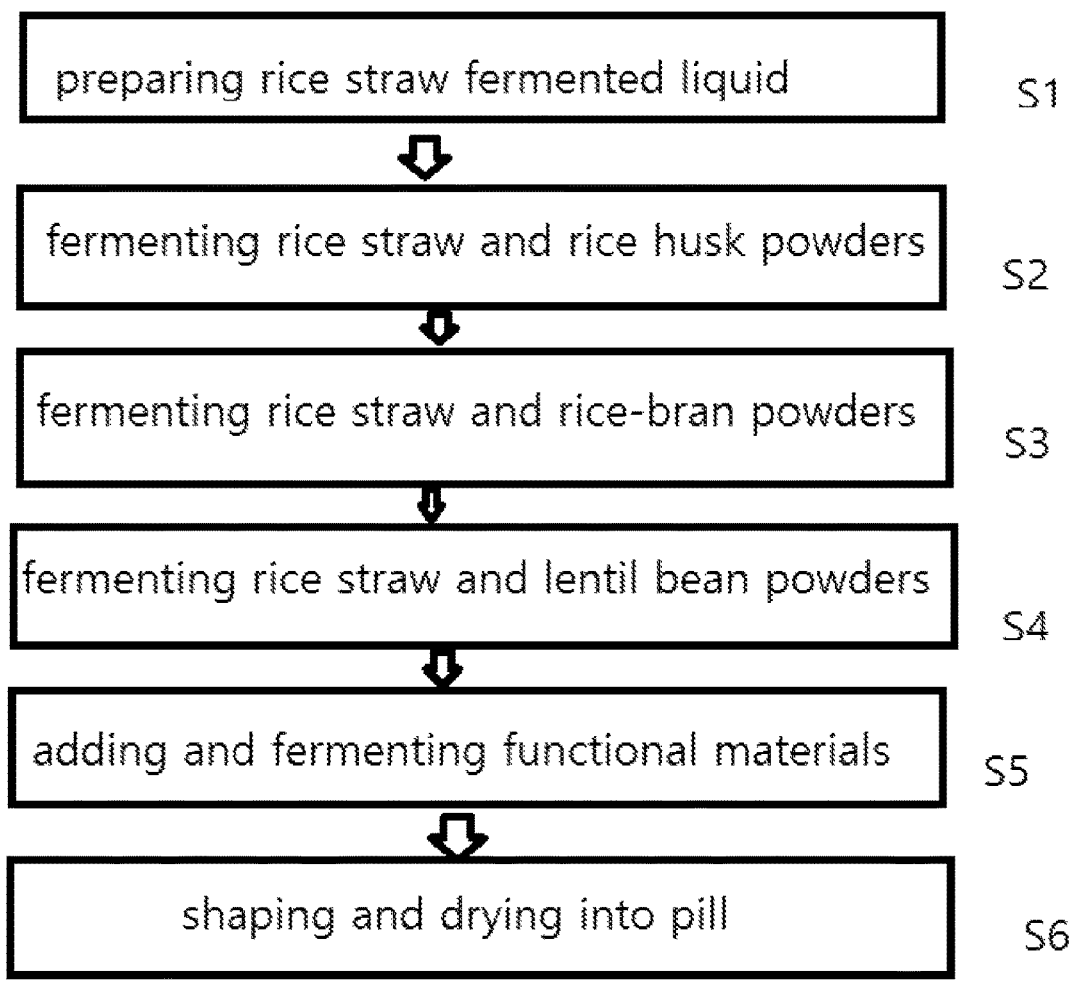

FERMENTED MINERAL RAW-EDIBLE PILL WITH CONSTIPATION REDUCTION AND FATIGUE RECOVERY AND METHOD FOR PRODUCING THE SAME

CROSS-REFERENCE TO RELATED APPLICATION

This application claims the benefit of Korea patent application No. 10-2015-0092978 filed on Jun. 30, 2015, the entire content of which is incorporated herein by reference for all purposes as if fully set forth herein.

BACKGROUND

Field of the Present Disclosure

The present disclosure relates to a fermented mineral raw-edible pill with constipation reduction and fatigue recovery and a method for producing the pill. More particularly, the present disclosure relates to a fermented mineral raw-edible pill with constipation reduction and fatigue recovery and a method for producing the pill, wherein a rice-husk powder, a rice-bran powder and a lentil bean power are fermented using *Bacillus subtilis* cultivated in the rice straw.

Discussion of the Related Art

Currently, people have constipation and obesity due to lack of beneficial microorganisms and excessive intake of fatty food. Recently, as a precautionary measure, a combination of a simple exercise and natural products are increasingly interested and thus research and development thereof has been actively conducted.

SUMMARY

The present inventor has studied and developed natural fermentation materials to improve health of the tired modern people and to be easily edible and mobile anywhere, anytime. In this effort, the present inventor has developed a fermented mineral raw-edible pill with constipation reduction and fatigue recovery and a method for producing the pill, wherein a rice-husk powder, a rice-bran powder and a lentil bean power are fermented using *Bacillus subtilis* cultivated in the rice straw.

The present disclosure provides a natural fermented food which may be easily portable and may be good at improving health of the stomach and be effective to reduce the constipation and obesity.

The present disclosure provides a method for producing a natural fermented food which may be easily portable and may be good at improving health of the stomach and be effective to reduce the constipation and obesity.

In an aspect of the present disclosure, there is provided a method for producing a fermented mineral raw-edible pill with constipation reduction and fatigue recovery, the method comprising:

(S1) mixing a nuruk, a finely-cut rice straw, and a barley malt with a water, wherein the nuruk 1 to 10 percentage by weight to obtain a first mixture, the barley malt 10 to 20 percentage by weight and the finely-cut rice straw 10 to 30 percentage by weight are based on the water 100 percentage by weight, and aging the first mixture at 26 to 35° C. for 2 to 4 day to acquire a rice straw fermented liquid;

(S2) mixing a rice straw powder and a rice-husk powder with each other at a mixing ratio 1:2 to 2:1 by weight to acquire a second mixture, and adding and kneading the second mixture into the rice straw fermented liquid produced from the step (S1) to acquire a third mixture, wherein the rice straw fermented liquid 20 to 60 percentage by weight is based on the second mixture 100 percentage by weight, and fermenting the third mixture at 35 to 45° C. for 65 to 75 hours, and drying the third mixture for 10 to 20 days in a shady place;

(S3) mixing a rice straw powder and a rice-bran powder with each other at a mixing ratio 1:2 to 2:1 by weight to acquire a fourth mixture, and adding and kneading the fourth mixture into a further rice straw fermented liquid produced from the step (S1) to acquire a fifth mixture, wherein the further rice straw fermented liquid 20 to 60 percentage by weight is based on the fourth mixture 100 percentage by weight, and fermenting the fifth mixture at 35 to 45° C. for 65 to 75 hours, and drying the fifth mixture for 10 to 20 days in a shady place;

(S4) mixing a rice straw powder and a lentil-bean powder with each other at a mixing ratio 1:2 to 2:1 by weight to acquire a sixth mixture, and adding and kneading the sixth mixture into a still further rice straw fermented liquid produced from the step (S1) to acquire a seventh mixture, wherein the still further rice straw fermented liquid 20 to 60 percentage by weight is based on the sixth mixture 100 percentage by weight, and fermenting the seventh mixture at 35 to 45° C. for 90 to 100 hours, and drying the seventh mixture for 10 to 20 days in a shady place;

(S5) mixing the third mixture, the fifth mixture and the seventh mixture with each other to acquire an eighth mixture, and adding the eighth mixture into a still further rice straw fermented liquid produced from the step (S1) along with bitter gourd powder, ginger powder, turmeric powder, dry laver powder, Eucommiaceae bark powder, onion powder, *Lentinus edodes* powder, Spikemoss powder, *Allium tuberosum* Rottler powder, sesame leaf powder, sea tangle powder and *Cornus Officinalis* powder to acquire a ninth mixture, wherein the still further rice straw fermented liquid 10 to 60 percentage, the bitter gourd powder 0.1 to 2 percentage by weight, the ginger powder 0.1 to 2 percentage by weight, the turmeric powder 0.05 to 1 percentage by weight, the dry layer powder 10 to 20 percentage by weight, the Eucommiaceae bark powder 0.1 to 2 percentage by weight, the onion powder 0.1 to 2 percentage by weight, the *Lentinus edodes* powder 0.1 to 2 percentage by weight, the Spikemoss powder 0.1 to 2 percentage by weight, the *Allium tuberosum* Rottler powder 0.1 to 2 percentage by weight, the sesame leaf powder 0.1 to 2 percentage by weight, the sea tangle powder 10 to 20 percentage by weight and the *Cornus Officinalis* powder 0.1 to 2 percentage by weight are based on the eighth mixture 100 percentage by weight, and fermenting the ninth mixture at 30 to 40° C. for 20 to 80 hours; and (S6) mixing and threading the fermented ninth mixture with glutinous rice powder, coconut oil and honey to acquire a tenth mixture, wherein the glutinous rice powder 1 to 10 percentage by weight, the coconut oil 1 to 5 percentage by weight and the honey 1 to 5 percentage by weight are based on the fermented ninth mixture 100 percentage by weight, and shaping and drying the tenth mixture into pills.

In one embodiment, mixing the rice straw powder and the rice-husk powder with each other comprises mixing the rice straw powder and the rice-husk powder with each other at a mixing ratio 1:1 by weight.

In one embodiment, mixing the rice straw powder and the rice-bran powder with each other comprises mixing the rice straw powder and the rice-bran powder with each other at a mixing ratio 1:1 by weight.

In one embodiment, wherein mixing the rice straw powder and the lentil-bean powder with each other comprises mixing the rice straw powder and lentil-bean powder with each other at a mixing ratio 1:1 by weight.

In an aspect of the present disclosure, there is provided a fermented mineral raw-edible pill with constipation reduction and fatigue recovery, wherein the pill is produced using the method.

In an aspect of the present disclosure, there is provided a method for producing a fermented mineral solid pill with constipation reduction and fatigue recovery, the method comprising: mixing and aging a nuruk, a finely-cut rice straw, and a barley malt with a water to acquire a rice straw fermented liquid; mixing and threading at least one of a rice-husk powder, a rice-bran powder and a lentil-bean powder into the rice straw fermented liquid produced from the step to acquire a mixture; and shaping and drying the mixture into pills.

In an aspect of the present disclosure, there is provided a fermented mineral solid pill with constipation reduction and fatigue recovery, wherein the pill is produced using the method.

In an aspect of the present disclosure, there is provided a method for producing a fermented mineral pill with constipation reduction and fatigue recovery, the method comprising: cultivating Bacillus subtilis using a rice straw; fermenting at least one of a rice-husk powder, a rice-bran powder and a lentil bean power using the Bacillus subtilis to acquire a fermented mixture; and shaping and drying the fermented mixture into solid pills.

The present fermented mineral raw-edible pill may be effective to reduce constipation and replenish the minerals and good microbes in the body, and, in particular, enhance the bowel movements. In addition, the mineral may help the bowel movement to heal the constipation. The fatty portion may disappear and the tiredness may disappear to lead to vitality to life. In addition, the present disclosure may be edible willingly anywhere anytime and easy to carry. Therefore, the fermented mineral raw-edible pill of the present disclosure may be expected to be used to promote health of the modern man and may be very useful as an energy pill that can help prevent illnesses.

BRIEF DESCRIPTIONS OF THE DRAWINGS

The accompanying drawing included to provide a further understanding of the present disclosure illustrates embodiments of the present disclosure.

The sole FIGURE shows a flow chart of a method for producing a fermented mineral raw-edible pill with constipation reduction and fatigue recovery in accordance with the present disclosure.

DETAILED DESCRIPTIONS

Examples of various embodiments are illustrated in the accompanying drawings and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

Example embodiments will be described in more detail with reference to the accompanying drawings. The present disclosure, however, may be embodied in various different forms, and should not be construed as being limited to only the illustrated embodiments herein. Rather, these embodiments are provided as examples so that this disclosure will be thorough and complete, and will fully convey the aspects and features of the present disclosure to those skilled in the art.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, s, operations, elements, and/or components, but do not preclude the presence or addition of one or more other features, integers, s, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure."

The present disclosure provides a fermented mineral raw-edible pill with constipation reduction and fatigue recovery wherein the pill material is fermented using Bacillus subtilis cultivated in a rice straw. The fermented mineral raw-edible pill with constipation reduction and fatigue recovery may be produced using the following steps:

(S1) mixing a nuruk, a finely-cut rice straw, and a barley malt with a water, wherein the nuruk 1 to 10 percentage by weight to obtain a first mixture, the barley malt 10 to 20 percentage by weight and the finely-cut rice straw 10 to 30 percentage by weight are based on the water 100 percentage by weight, and aging the first mixture at 26 to 35° C. for 2 to 4 day to acquire a rice straw fermented liquid;

(S2) mixing a rice straw powder and a rice-husk powder with each other at a mixing ratio 1:2 to 2:1 by weight to acquire a second mixture, and adding and kneading the second mixture into the rice straw fermented liquid produced from the step (S1) to acquire a third mixture, wherein the rice straw fermented liquid 20 to 60 percentage by weight is based on the second mixture 100 percentage by weight, and fermenting the third mixture at 35 to 45° C. for 65 to 75 hours, and drying the third mixture for 10 to 20 days in a shady place;

(S3) mixing a rice straw powder and a rice-bran powder with each other at a mixing ratio 1:2 to 2:1 by weight to acquire a fourth mixture, and adding and kneading the fourth mixture into a further rice straw fermented liquid produced from the step (S1) to acquire a fifth mixture, wherein the further rice straw fermented liquid 20 to 60 percentage by weight is based on the fourth mixture 100 percentage by weight, and fermenting the fifth mixture at 35 to 45° C. for 65 to 75 hours, and drying the fifth mixture for 10 to 20 days in a shady place;

(S4) mixing a rice straw powder and a lentil-bean powder with each other at a mixing ratio 1:2 to 2:1 by weight to acquire a sixth mixture, and adding and kneading the sixth mixture into a still further rice straw fermented liquid produced from the step (S1) to acquire a seventh mixture, wherein the still further rice straw fermented liquid 20 to 60 percentage by weight is based on the sixth mixture 100 percentage by weight, and fermenting the seventh mixture at 35 to 45° C. for 90 to 100 hours, and drying the seventh mixture for 10 to 20 days in a shady place;

(S5) mixing the third mixture, the fifth mixture and the seventh mixture with each other to acquire an eighth mixture, and adding the eighth mixture into a still further rice straw fermented liquid produced from the step (S1) along with bitter gourd powder, ginger powder, turmeric powder, dry laver powder, Eucommiaceae bark powder, onion powder, *Lentinus edodes* powder, Spikemoss powder, *Allium tuberosum* Rottler powder, sesame leaf powder, sea tangle powder and *Cornus Officinalis* powder to acquire a ninth mixture, wherein the still further rice straw fermented liquid 10 to 60 percentage, the bitter gourd powder 0.1 to 2 percentage by weight, the ginger powder 0.1 to 2 percentage by weight, the turmeric powder 0.05 to 1 percentage by weight, the dry layer powder 10 to 20 percentage by weight, the Eucommiaceae bark powder 0.1 to 2 percentage by weight, the onion powder 0.1 to 2 percentage by weight, the *Lentinus edodes* powder 0.1 to 2 percentage by weight, the Spikemoss powder 0.1 to 2 percentage by weight, the *Allium tuberosum* Rottler powder 0.1 to 2 percentage by weight, the sesame leaf powder 0.1 to 2 percentage by weight, the sea tangle powder 10 to 20 percentage by weight and the *Cornus Officinalis* powder 0.1 to 2 percentage by weight are based on the eighth mixture 100 percentage by weight, and fermenting the ninth mixture at 30 to 40° C. for 20 to 80 hours; and (S6) mixing and threading the fermented ninth mixture with glutinous rice powder, coconut oil and honey to acquire a tenth mixture, wherein the glutinous rice powder 1 to 10 percentage by weight, the coconut oil 1 to 5 percentage by weight and the honey 1 to 5 percentage by weight are based on the fermented ninth mixture 100 percentage by weight, and shaping and drying the tenth mixture into pills.

As used herein, the term, "*Bacillus subtilis*" is Gram-positive genus belonging to *Bacillus*. Since the *Bacillus subtilis* is free of LPS and endotoxin present in the Gram-negative bacteria, it may be used in food and medicines. It may have GRAS grade passing the FDA's safety test. It may have the shorter production time of virus-like particles as compared to existing insect cells. It may be efficiently and well developed in a normal incubator and the use of the *Bacillus subtilis* may be safer than using *E. coli*.

As used herein, the term "nuruk" may refer to a fermentation agent used in producing an alcohol liquor. It may be made from a dough made of coarsely-ground grain and water naturally inoculated with bacteria, fungi, yeast, and lactic add bacteria. It jump-starts the fermentation process and helps making a fermented alcohol beverage.

In the present disclosure, mineral fermentation may be achieved using the *Bacillus subtilis* cultivated in the rice straw using the traditional method. The fermented mineral raw-edible pill produced in accordance with the present disclosure may supplement the body with the mineral and act as the microbial supplements. Particularly, the pill may improve bowel movements and thus may allow the nutrients in food eaten every day to be absorbed into the body effectively. The microbes thereof may function as immune enhancement supplement. In addition, the minerals may help the bowel movement such that the constipation is reduced and the fat in the abdomen is reduced. The pill may allow the obesity to disappear and can allow the lift fatigue to disappear. The food digestibility is getting better, and the urine comes out well, and BP (blood pressure) ma be normalized. In addition, the face becomes smaller and becomes less wrinkled.

In the present disclosure, the rice straw fermented liquid containing *Bacillus subtilis* cultured from the rice straw may be used as an initial fermented liquid. In this connection, the rice straw fermented liquid may be produced by mixing a nuruk, a finely-cut rice straw, and a barley malt with a water, wherein the nuruk 1 to 10 percentage by weight to obtain a first mixture, the barley malt 10 to 20 percentage by weight and the finely-cut rice straw 10 to 30 percentage by weight are based on the water 100 percentage by weight, and aging the first mixture at 26 to 35° C. for 2 to 4 day.

In the present disclosure, the rice-husk powder may be produced by grinding the rice-husk into a size of 0.1 to 3 mm. The rice-husk powder and rice straw powder may be mixed with each other at a mixing ratio 1:2 to 2:1 by weight. A mixing ratio range out of this range may not be suitable for fermentation and dry of the rice straw fermented liquid.

In the present disclosure, the rice-bran powder may improve an immune power and function as a good anti-cancer agent. The rice-bran powder and rice straw powder may be mixed with each other at a mixing ratio 1:2 to 2:1 by weight. A mixing ratio range out of this range may not be suitable for fermentation and dry of the rice straw fermented liquid.

In the present disclosure, the lentil bean may contain various nutrients such as a protein and dietary fiber and potassium and B vitamins and folic acid and iron to have excellent antioxidant properties. Since the lentil bean has high protein and fiber content, it may allow the immunity enhancement, may prevent the cardiovascular sickness due to a reduction of cholesterol levels, and may have anti-aging, and anti-cancer activities. In addition, a large amount of iron and folic acid contained therein is also effective in anemia. In addition, it may have been spotlighted as high protein and low-calorie foods and as a diet food that relieve constipation and indigestion due to its dietary fiber content large as 10 times as that of bananas. In the present disclosure, the lentil bean powder may be produced by grinding the lentil bean into a size of 0.1 to 3 mm. The lentil bean powder and rice straw powder may be mixed with each other at a mixing ratio 1:2 to 2:1 by weight. A mixing ratio range out of this range may not be suitable for fermentation and dry of the rice straw fermented liquid.

In the present disclosure, the rice-husk powder, rice-bran powder and lentil bean powder may be fermented using *Bacillus subtilis*-containing rice straw fermented liquid. Then, to the mixture of the rice-husk powder, rice-bran powder and lentil bean powder fermented using *Bacillus subtilis*-containing rice straw fermented liquid, various following functional materials for the raw-edible pill may be added: the bitter gourd powder, ginger powder, turmeric powder, dry laver powder, Eucommiaceae bark powder, onion powder, *Lentinus edodes* powder, Spikemoss powder, *Allium tuberosum* Rottler powder, sesame leaf powder, sea tangle powder and *Cornus Officinalis* powder. Then, the resulting mixture may be again fermented in the rice straw fermented liquid.

In this connection, the bitter gourd powder, ginger powder, turmeric powder, dry laver powder, eucommiaceae bark powder, onion powder, *lentinus edodes* powder, spikemoss powder, *Allium tuberosum* Rottler powder, sesame leaf powder, sea tangle powder and *Cornus Officinalis* powder may be commercially available. The mixture of the rice-husk powder, rice-bran powder and lentil bean powder fermented using *Bacillus subtilis*-containing rice straw fermented liquid may be referred to as "multi-functional mixture" as used herein. The bitter gourd powder 0.1 to 2 percentage by weight, the ginger powder 0.1 to 2 percentage by weight, the turmeric powder 0.05 to 1 percentage by weight, the dry laver powder 10 to 20 percentage by weight, the Eucommiaceae bark powder 0.1 to 2 percentage by weight, the onion powder 0.1 to 2 percentage by weight, the *Lentinus edodes* powder 0.1 to 2 percentage by weight, the Spikemoss powder 0.1 to 2 percentage by weight, the *Allium tuberosum* Rottler powder 0.1 to 2 percentage by weight, the sesame leaf powder 0.1 to 2 percentage by weight, the sea tangle powder 10 to 20 percentage by weight and the *Cornus Officinalis* powder 0.1 to 2 percentage by weight are based on the multi-functional mixture 100 percentage by weight.

In the present disclosure, the bitter gourd powder is rich in a natural plant-extracted insulin to lower blood glucose levels and activate the pancreatic function to be known as a good food for diabetes. In the present disclosure, a bitter gourd powder may be produced by grinding the bitter gourd fruit to a size of 0.1 to 3 mm.

In the present disclosure, the ginger contains proteolytic enzymes to stimulate the secretion of digestive juices and promote bowel movements to treat nausea and diarrhea. The gingerols or shogaols therein may have strong anti-bacteria activity against various pathogenic bacteria such as especially typhoid bacteria or a cholera. In the present disclosure, a ginger powder may be produced by grinding the ginger to a size of 0.1 to 3 mm.

In the present disclosure, the turmeric may be good at healing a menstrual pain and at relieving the pain of bruises and sprains. The turmeric may allow the memory power to be higher. In addition, the component of turmeric is curcumin which has an anti-cancer effect and has a liver detoxification function. In the present disclosure, a turmeric powder ground to a size of 0.1 to 3 mm may be employed.

In the present disclosure, the dry layer may have a large amount of iron and thus may be known to have a superior antioxidant effect and may be a vitamin A-rich alkaline food. In the present disclosure, a dry layer powder ground to a size of 0.1 to 3 mm may be employed.

In the present disclosure, the Eucommiaceae bark may contain various components such as an organic acid, chlorogenic acid, vitamin C, alkaloids, rubber, etc. The component seen as white when the bark is cut (named gutta-percha) may have blood pressure lowering effect, liver and kidney protection effect, muscle and bone strength effect, fetus protection effect, healing of a waste pain resulting from the poor kidney. In the present disclosure, the Eucommiaceae bark powder pulverized to a size of 0.1 to 3 mm may be employed.

In the present disclosure, the onion may have quercetins serving to prevent blood vessels from becoming stiff or narrowed due to cholesterol. The onion may be effective to remove the cholesterol or high blood pressure. There is also the ability to suppress harmful free radicals to prevent aging promotion. In the present disclosure, the onion powder ground to a size of 0.1 to 3 mm may be employed.

In the present disclosure, the *Lentinus edodes* may be effective to prevent the cancer, hypertension, diabetes, and osteoporosis. In the present disclosure, the *Lentinus edodes* powder ground to a size of 0.1 to 3 mm may be employed.

In the present disclosure, the Spikemoss is known to have the effect of removing the toxin from the body and to be very prominent to treat gynecological problems of women. In the present disclosure, the spikemoss powder ground to a size of 0.1 to 3 mm may be employed.

In the present disclosure, the *Allium tuberosum* Rottler is rich in vitamins A and C. Most of the saccharides contained in *Allium tuberosum* Rottler may be monosaccharides of the glucose and fructose. The *Allium tuberosum* Rottler has a tonic effect similar to garlic. In the present disclosure, the *Allium tuberosum* Rottler powder ground to a size of 0.1 to 3 mm may be employed.

In the present disclosure, the sesame leaf contains the iron much as twice as the spinach. The sesame leaf contains nutritious minerals such as calcium and vitamin A and vitamin C in an abundant amount. Chlorophyll is effective in digestive disorders of anorexia and diarrhea, constipation, etc. The sesame leaf contains the vitamin K which acts to coagulate bloods. The sesame leaf is known to also help prevent cancer, and various adult diseases. In the present disclosure, the sesame leaf powder pulverized to a size of 0.1 to 3 mm may be employed.

In the present disclosure, the sea tangle may help constipation by increasing the amount of bowel movements. An alginic acid rich in the sea tangle also interferes with the absorption of fat. In the present disclosure, a sea tangle powder ground to a size of 0.1 to 3 mm may be employed.

In the present disclosure, the *Cornus Officinalis* is the fruit of the trees of the deciduous tall tree of *Cornus Officinalis* cornaceae. It is at first a green nucleus of the oval and is red ripen in August-October. The fruit has glycosides such as cornin, Morroniside, Loganin, tannin, Saponin and an organic acid such as wine acid, malic acid, tartaric acid. In addition, there is also plenty of vitamin A. The seed thereof contains palmitic acid, oleic acid, linoleic acid and the like. The cornin may be known to have the action of the parasympathetic nervous excitement. The *Cornus Officinalis* may be effective to heal the headache, tinnitus, consumption, fever, menorrhagia, etc. As the folk medicine, the *Cornus Officinalis* may be used for a cold sweat, and enuresis. In the present disclosure, the *Cornus Officinalis* powder ground to a size of 0.1 to 3 mm may be employed.

In addition, the present fermented mineral raw-edible pill may have glutinous rice powders, coconut oil and honey to allow the mixture to be shaped into the solid pill.

The fermented mineral raw-edible pill as prepared in accordance with the present disclosure may allow the constipation reduction and fatigue recovery. The fermented mineral raw-edible pill may act as the bone mineral and microbial supplements, and, may particularly allow the bowel movements to be well. The pill contains the number of beneficial microorganisms to promote an immune power. In addition, the minerals therein help in bowel movement to reduce the constipation. The pill may allow the fatty substance in the abdomen to be discharged out of the body to prevent the obesity and may cause tiredness to disappear to lead to vitality to life. In addition, the fermented mineral raw-edible pill of the present disclosure may be edible willingly anywhere anytime and easy to carry. Therefore, in the present disclosure, the recovery fermented mineral raw-edible pill with the constipation reduction and fatigue enables a modern adult disease prevention and the promotion of a health.

Embodiment 1

First, the nuruk 100 g, barley malt 400 g and finely-cut rice straw 500 g are added into water 3 L and are mixed and aged at 30° C. for 3 day to acquire a rice straw fermented liquid.

Then, a rice straw powder 16 g and rice-husk powder 16 g are mixed with each other. The mixture is added into the rice straw fermented liquid 10 g. The resulting material is threaded and is fermented at 40° C. for 70 hours, and then is dried for 15 in a shady place. Thus, the fermented rice-husk mixture is obtained.

Further, a rice straw powder 16 g and rice-bran powder 16 g are mixed with each other. The mixture is added into the rice straw fermented liquid 10 g. The resulting material is threaded and is fermented at 40° C. for 70 hours, and then is dried for 15 in a shady place. Thus, the fermented rice-bran mixture is obtained.

Further, a rice straw powder 16 g and lentil bean powder 16 g are mixed with each other. The mixture is added into the rice straw fermented liquid 10 g. The resulting material is threaded and is fermented at 40° C. for 70 hours, and then is dried for 15 in a shady place. Thus, the fermented lentil bean mixture is obtained.

Thereafter, the fermented rice-husk, rice-bran and lentil bean mixtures are mixed with each other. Into this resulting mixture, a rice straw fermented liquid 30 g, bitter gourd powder 0.4 g, ginger powder 0.4 g, turmeric powder 0.1 g, dry laver powder 16 g, eucommiaceae bark powder 0.4 g, onion powder 0.7 g, *lentinus edodes* powder 0.4 g, spike-moss powder 0.4 g, *Allium tuberosum* Rottler powder 0.4 g, sesame leaf powder 0.4 g, sea tangle powder 16 g and *Cornus Officinalis* powder 0.4 g are added. Then, the resulting mixture is dried 35° C. for 24 hours to acquire the fermented multi-functional mixture.

Into the fermented multi-functional mixture, a glutinous rice powder, coconut oil and honey are added and then threaded. The resulting product is shaped and dried into the pill.

Example 1

Five females in twenties having chronic constipations consume the present fermented mineral raw-edible pills 30 g produced as in the embodiment 1 per day for three weeks. Improvement in constipation was observed. In this connection, the subjects all were instructed to have the same diet. The evaluation points may be scored as follows: 9 point: very good; 7 point: good; 5 point: usually; 3 point: slightly bad; 1 point: very bad point). Sensory evaluation verifies a significant difference between the respective samples at 5% ANOVA level using the Duncan's multiple range test. The results are shown in Table 1:

TABLE 1

|  | subject 1 | subject 2 | subject 3 | subject 4 | subject 5 |
| --- | --- | --- | --- | --- | --- |
| 1 week | 5 | 5 | 4 | 5 | 4 |
| 2 weeks | 7 | 6 | 6 | 7 | 6 |
| 3 weeks | 9 | 8 | 8 | 9 | 9 |

It is proved as shown in the table 1 that the present fermented mineral raw-edible pills are effective to reduce the constipation of all subjects.

Example 2

Five males in forties having chronic fatigues consume the present fermented mineral raw-edible pills 30 g produced as in the embodiment 1 per day for four weeks. Improvement in fatigue was observed. In this connection, the subjects all were instructed to have the same diet. The evaluation points may be scored as follows: 9 point: very good; 7 point: good; 5 point: usually; 3 point: slightly bad; 1 point: very bad). The results are shown in Table 2:

TABLE 2

|  | subject 1 | subject 2 | subject 3 | subject 4 | subject 5 |
| --- | --- | --- | --- | --- | --- |
| 2 weeks | 6 | 6 | 6 | 7 | 6 |
| 3 weeks | 8 | 8 | 9 | 9 | 7 |

It is proved as shown in the table 2 that the present fermented mineral raw-edible pills are effective to relieve the fatigue of all subjects.

Further, the male and female subjects are good at discharging urine, and have a good digestion and have a non-high pressure state.

What is claimed is:

1. A method for producing a fermented mineral raw-edible pill with constipation reduction and fatigue recovery, the method comprising:
   (S1) mixing nuruk, finely-cut rice straw, and barley malt with water, wherein the nuruk 1 to 10 percentage by weight, the barley malt 10 to 20 percentage by weight and the finely-cut rice straw 10 to 30 percentage by weight are based on the water 100 percentage by weight to obtain a first mixture, and aging the first mixture at 26 to 35° C. for 2 to 4 days to acquire a rice straw fermented liquid;
   (S2) mixing rice straw powder and rice-husk powder with each other at a mixing ratio 1:2 to 2:1 by weight to acquire a second mixture, and adding and kneading the second mixture into the rice straw fermented liquid produced from the step (S1) to acquire a third mixture, wherein the rice straw fermented liquid 20 to 60 percentage by weight is based on the second mixture 100 percentage by weight, and fermenting the third mixture at 35 to 45° C. for 65 to 75 hours, and drying the third mixture for 10 to 20 days in a shady place;
   (S3) mixing the rice straw powder and rice-bran powder with each other at a mixing ratio 1:2 to 2:1 by weight to acquire a fourth mixture, and adding and kneading the fourth mixture into the rice straw fermented liquid produced from the step (S1) to acquire a fifth mixture, wherein the rice straw fermented liquid 20 to 60 percentage by weight is based on the fourth mixture 100 percentage by weight, and fermenting the fifth mixture at 35 to 45° C. for 65 to 75 hours, and drying the fifth mixture for 10 to 20 days in a shady place;

(S4) mixing the rice straw powder and lentil-bean powder with each other at a mixing ratio 1:2 to 2:1 by weight to acquire a sixth mixture, and adding and kneading the sixth mixture into the rice straw fermented liquid produced from the step (S1) to acquire a seventh mixture, wherein the rice straw fermented liquid 20 to 60 percentage by weight is based on the sixth mixture 100 percentage by weight, and fermenting the seventh mixture at 35 to 45° C. for 90 to 100 hours, and drying the seventh mixture for 10 to 20 days in a shady place;

(S5) mixing the third mixture, the fifth mixture and the seventh mixture with each other to acquire an eighth mixture, and adding the eighth mixture into the rice straw fermented liquid produced from the step (S1) along with bitter gourd powder, ginger powder, turmeric powder, dry laver powder, Eucommiaceae bark powder, onion powder, *Lentinus edodes* powder, Spikemoss powder, *Allium tuberosum* Rottler powder, sesame leaf powder, sea tangle powder and *Cornus Officinalis* powder to acquire a ninth mixture, wherein the rice straw fermented liquid 10 to 60 percentage, the bitter gourd powder 0.1 to 2 percentage by weight, the ginger powder 0.1 to 2 percentage by weight, the turmeric powder 0.05 to 1 percentage by weight, the dry laver powder 10 to 20 percentage by weight, the Eucommiaceae bark powder 0.1 to 2 percentage by weight, the onion powder 0.1 to 2 percentage by weight, the *Lentinus edodes* powder 0.1 to 2 percentage by weight, the Spikemoss powder 0.1 to 2 percentage by weight, the *Allium tuberosum* Rottler powder 0.1 to 2 percentage by weight, the sesame leaf powder 0.1 to 2 percentage by weight, the sea tangle powder 10 to 20 percentage by weight and the *Cornus Officinalis* powder 0.1 to 2 percentage by weight are based on the eighth mixture 100 percentage by weight, and fermenting the ninth mixture at 30 to 40° C. for 20 to 80 hours; and (S6) mixing and threading the fermented ninth mixture with glutinous rice powder, coconut oil and honey to acquire a tenth mixture, wherein the glutinous rice powder 1 to 10 percentage by weight, the coconut oil 1 to 5 percentage by weight and the honey 1 to 5 percentage by weight are based on the fermented ninth mixture 100 percentage by weight, and shaping and drying the tenth mixture into pills.

2. The method of claim 1, wherein mixing the rice straw powder and the rice-husk powder with each other comprises mixing the rice straw powder and the rice-husk powder with each other at a mixing ratio 1:1 by weight.

3. The claim 1, wherein mixing the rice straw powder and the rice-bran powder with each other comprises mixing the rice straw powder and the rice-bran powder with each other at a mixing ratio 1:1 by weight.

4. The claim 1, wherein mixing the rice straw powder and the lentil-bean powder with each other comprises mixing the rice straw powder and the lentil-bean powder with each other at a mixing ratio 1:1 by weight.

5. A fermented mineral raw-edible pill with constipation reduction and fatigue recovery, wherein the pill is produced using the method of claim 1.

* * * * *